United States Patent [19]

Wadsworth

[11] Patent Number: 5,027,456
[45] Date of Patent: Jul. 2, 1991

[54] GENTLE RESTRAINT FOR IN-BED PATIENT

[76] Inventor: Jewell Wadsworth, 244 Southorne, Mesa, Ariz. 85204

[21] Appl. No.: 447,921

[22] Filed: Dec. 8, 1989

[51] Int. Cl.⁵ .......................... A61F 6/37; A47G 9/02
[52] U.S. Cl. ......................................... 5/424; 5/494; 128/872
[58] Field of Search ................... 5/486, 494, 498, 424; 128/872, 873

[56] References Cited

U.S. PATENT DOCUMENTS

| | | | |
|---|---|---|---|
| 757,256 | 4/1904 | Brown | 5/498 |
| 2,789,292 | 4/1957 | Budinquest | 5/494 X |
| 3,530,487 | 9/1970 | Beer | 5/494 X |
| 3,696,450 | 10/1972 | Dupler | 5/486 |
| 3,857,124 | 12/1974 | Hadley | 5/494 X |
| 4,214,328 | 7/1980 | Custer, Jr. et al. | 5/494 |
| 4,301,561 | 11/1981 | McLeod | 5/498 X |
| 4,411,034 | 10/1983 | Williams | 5/494 |
| 4,742,821 | 5/1988 | Wooten | 128/873 |
| 4,853,996 | 8/1989 | Harrigan | 5/494 |

Primary Examiner—Michael F. Trettel
Attorney, Agent, or Firm—James F. Duffy

[57] ABSTRACT

A gentle restraint for use in inhibiting a person from leaving a bed, either accidentally or intentionally. The restraining forces are provided by a resilient covering which yields and stretches in accord with the movements and position of a person lying in the bed under the restraint. The yieldable restraint is provided by a resilient, open mesh covering which permits the free passage of air and water vapor and therefore does not entrap heat about the body of the person restrained.

9 Claims, 1 Drawing Sheet

GENTLE RESTRAINT FOR IN-BED PATIENT

FIELD OF THE INVENTION

The invention relates to means for providing a gentle restraining force to restrain a non-violent person from falling from or otherwise leaving a bed. In particular, the invention relates to a stretchably yieldable restraint covering which provides gentle restraint without immobilizing a person on a bed.

PRIOR ART

The prior art is replete with devices for preventing children or elderly persons from falling from a bed or kicking off the blanket coverings while sleeping. Mendyk, in U.S. Pat. No. 4,241,466, issued Dec. 30, 1980 discloses a safety bed sheet for these purposes. The safety bed sheet is in the form of a fitted bottom and a superposed top sheet the same width as the bottom sheet's upper surface but shortened at the head and foot end of the safety sheet. The top and bottom sheets are coupled together along their, longitudinal, marginal edges with the coupling at one edge being releasable to permit entry and exit of a person from between the two sheets. Many persons experience difficulty sleeping when a sheet is drawn tightly cross their body as is the situation which results from use of the Mendyk invention.

In U.S. Pat. No. 4,653,131, issued to Diehl on Mar. 31, 1987, a restraint, in the form of a fabric sheet, is provided which is coupled at its edges to the frame of the bed in which a patient lies supine. An opening in the fabric sheet is provided for the head of the patient. In one suggested embodiment of the invention, a turtleneck-like opening is provided in the tautly drawn fabric sheet to provide egress for the patient's head. A person, to which such restraint is applied, experiences a sense of total loss of freedom. Such a sense of loss may drastically change the aspect of a person from one of gentle compliance to one of violent rebellion. And certainly, being so trussed up in such an all-encompassing restraint has an adverse affect on the ability to obtain a restful night's sleep.

A coverlet having head and foot ends free with its longitudinal sides drawn snugly to a mattress is disclosed in U.S. Pat. No. 3,134,110, issued to Gamichon on May 26, 1964. Straps, passing beneath the mattress, draw the coverlet down tautly over the body of the person reclining on the mattress. Zipper fasteners permit removal of the coverlet from the restraining strap assembly.

There is a sense of security, generated from loving childhood experiences, in being snugly tucked into bed. However, when bedding is tucked in at the sides of the mattress, there is sufficient give and take in the coupling of the covering and the mattress to obviate any sense of captivity within the restraining embrace of the covering. A person "tucked into bed" may move from side to side beneath the bed coverings. More importantly, a person so "tucked in" may roll upon the mattress from one sleeping position to another. While much of the prior art directed to restraining a person in a bed will permit the restrained person to move from side to side, the unyielding restraint of a tautly drawn sheet or cover tends to inhibit a person from rolling from one sleeping position to another. When a restraint not only inhibits a person from leaving a bed but tends to prevent free movement on the bed in the course of the night's sleep, a sense of dread and captivity is engendered within the person. At the very least, a restful night's sleep is inhibited; and, with certain patients, panic is engendered. Such difficulties are even further compounded in the type of restraint suggested by Diehl wherein even the position of a patient's head and shoulders is determined by the restraint applied to the patient.

It is the intent of the invention to provide a gentle restraint so as to inhibit a person from leaving a bed. Such gentle restraint will be herein disclosed as one which provides a yieldable restraining force on the body of a person lying in bed.

SUMMARY OF THE INVENTION

The invention is seen as an improvement over earlier inventions in that it provides a restraining force upon a supine person lying on a mattress such that the force yields to the movement and the change of position of the person. The restraint, therefore, is defined as a gentle restraint herein. The invention is claimed as the improvement over a bed having a mattress and a frame for supporting the mattress. The improvement is shown to comprise a gentle restraining means for restraining a non-violent person in a generally supine position on the mattress. The gentle restraining means itself is disclosed as a resilient covering which is yieldably and stretchingly drawn over a person lying on the mattress. Means are provided for coupling the resilient covering to the mattress so as to yieldingly restrain a person over which the resilient covering is drawn.

In a preferred embodiment of the invention, the resilient covering is a resilient, open mesh material through which air and water vapor may readily pass. These characteristics prevent heat entrapment about the body of a person being restrained by the resilient covering.

So that the resilient covering may be readily removed from the patient or completely removed from the mattress for laundering, etc., coupling means are provided to releasably couple the resilient covering to the mattress.

In an embodiment of the invention disclosed, the coupling means comprises a base positioned beneath the mattress. Walls rise from the base to at least partially encompass two sides and the foot of the mattress. Releasable coupling means then couple the walls to three sides of the resilient covering.

In prior art devices, the means whereby the restraints are coupled to the bed frame increased the degree of restraint applied to the person on the mattress who was being restrained. In the instant invention, means are provided for releasably coupling the base to the frame without increasing the level of restraint applied to the person on the mattress.

A DETAILED DESCRIPTION OF THE INVENTION

Figures 1, 2:
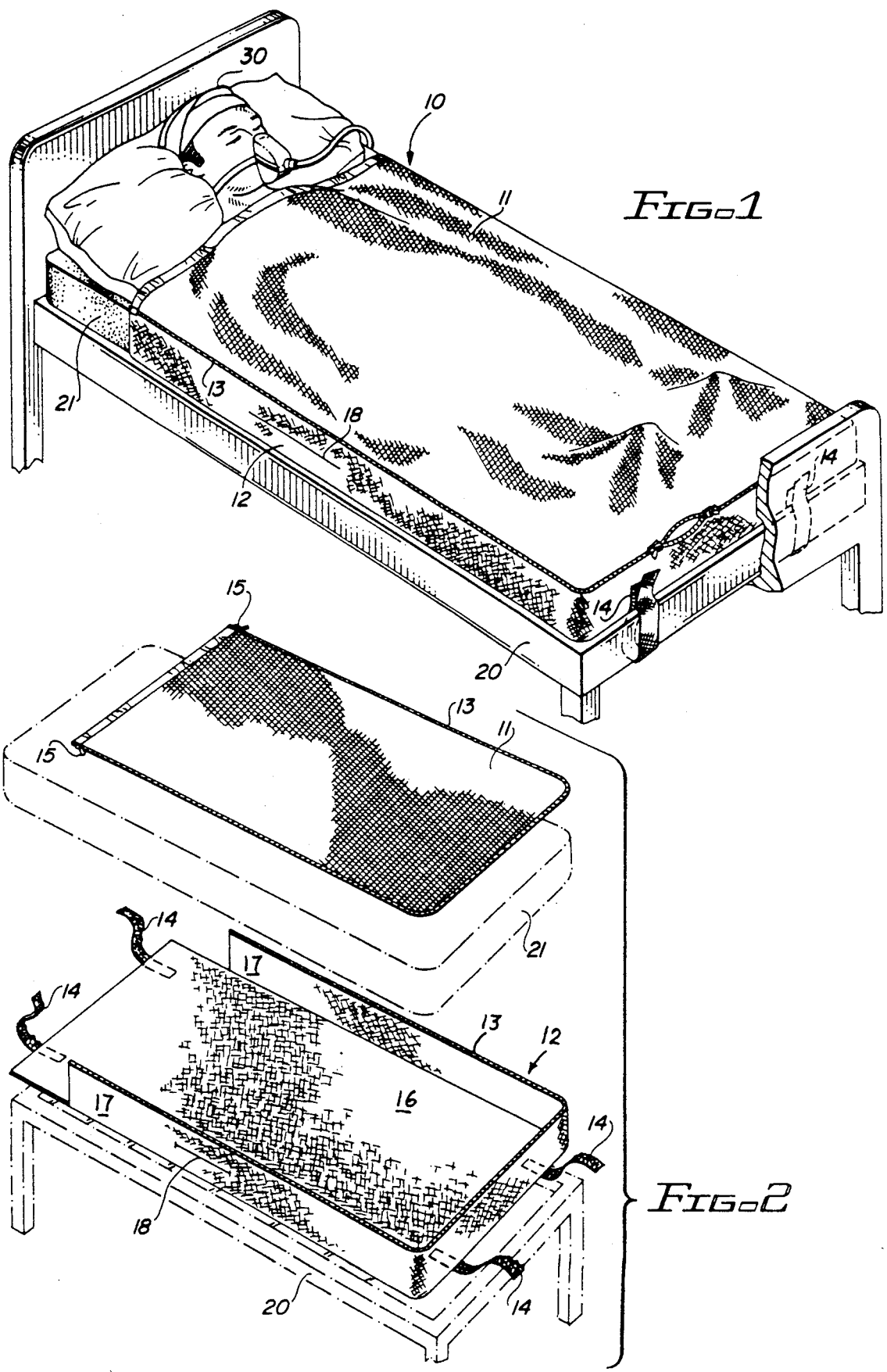
FIG. 1 illustrates the invention in use on a bed in which a patient is resting.
FIG. 2 is an exploded assembly view of the invention showing the mattress and frame of the bed in phantom outline.

For purposes of promoting an understanding of the principles of the invention, reference will now be made to the embodiments illustrated in the drawings and specific language will be used to describe same. It will nevertheless be understood that no limitation of the scope of the invention is thereby intended, there being contemplated such alterations and modifications of the illustrated device, and such further applications of the principles of the invention as disclosed herein, as would normally occur to one skilled in the art to which the invention pertains.

In FIG. 1, the gentle restraint is designated by reference 10. The restraint is referred to as a "gentle restraint" because the restraining forces applied to a person are yieldably subject to the movements of the person and the position assumed by the person within the bed.

In FIG. 1, a patient 30 lies supine upon a mattress 21 which is supported by bed frame 20. In addition to any conventional bed coverings which may be utilized to cover the patient 30, a resilient covering 11 is drawn over the supine patient 30. Resilient covering 11 provides a gentle restraining force upon the body of patient 30 in that it yields and stretches to accommodate the movement of the patient and the positions assumed by the patient while the patient is in bed.

To prevent heat entrapment about the body of patient 30, resilient covering 11 is made of an open weave material which permits the free passage of air and water vapor. Thus, the use of restraint 10 has little affect on maintaining or establishing the temperature comfort level of the patient. Such comfort level is more properly determined by room environmental temperature controls or by insulative type coverings conventionally employed as bedding materials. A convenient material which yields and stretches and provides an open weave breathable restraint is a material such as is often found in use with children's playpens. No limitation is herein intended by suggesting the use of the open mesh, playpen material as the resilient covering 11. Those skilled in the art will conceive of other resilient, breathable fabrics, or the like which will admirably serve the purposes herein espoused: the use of a resilient, yieldable, stretchable open weave material to apply a gentle restraint to a supine person such as to leave that person with a sense of security such as was engendered when, as a child, the person was tucked into bed by a parent or other loving individual.

The details and functioning of the invention are best understood with reference to both FIGS. 1 and 2. In FIG. 2, in exploded assembly view, the gentle restraint 10 is seen to comprise the resilient covering 11 and a semi-sheath 12 which partially encompasses mattress 21. Mattress 21 and bed frame 20 are not part of the invention and are therefore illustrated in phantom outline in FIG. 2.

Semi-sheath 12 may be made of any suitable material and comprises a base 16 and walls 17. Mattress 21 lays atop base 16 and the walls 17 rise upward adjacent to the sides of mattress 21.

Semi-sheath 12 is maintained in position on bed frame 20 by coupling means, here illustrated as straps 14, which may be secured in any conventional well known manner as, for example, by the use of hook and loop fasteners, not illustrated.

It should be well noted that strap 14, while coupling semi-sheath 12 to bed frame 20, has no influence on the degree of restraint applied to a person over which resilient covering 11 is drawn.

Resilient covering 11 is coupled to semi-sheath 12 by means of releasable couplings, here illustrated as zipper fastener 13. Mating portions of zipper fastener 13 are found on both resilient covering 11 and semi-sheath 12. Slides 15 releasably couple the mating sections of zipper 13 so as to provide releasable coupling means between resilient covering 11 and semi-sheath 12.

As indicated in FIG. 1, zipper slides 15 may be drawn together to fully couple resilient covering 11 to the foot of semi-sheath 12. However, the space illustrated between slide fasteners 15 in FIG. 1 suggest that the restraint applied at the feet of a person lying in bed may be controlled, or eliminated, by the degree to which slides 15 are drawn into juxtaposition.

In many instances, the gentle restraint 10 will be utilized with a patient who has been catheterized. An opening 18 is provided in one or more sides 17 of semi-sheath 12 to permit entry and egress of tubes utilized with the catheter.

When resilient covering 11 is drawn over patient 30 and zipper slides 15 moved to couple zipper sections 13 together, resilient covering 11 will yieldably and stretchingly cover that patient with a restraining force which is gentle enough to permit the patient to move not only from side to side but to roll from one position to another. The degree of restraint is suggestive of that experienced when bedding is tucked in at the sides of a mattress. With the use of gentle restraint 10, a person does not feel captured, but rather, secure.

What has been described is a gentle restraint for use in inhibiting a person from leaving a bed, either accidentally or intentionally. The restraining forces are provided by a resilient covering which yields and stretches in accord with the movements and position of a person lying on the bed under the restraint. The yieldable restraint is provided by a resilient, open mesh covering which permits the free passage of air and water vapor and therefore does not entrap heat about the body of the person restrained.

Those skilled in the art will conceive of other embodiments of the invention which may be drawn from the disclosure herein. To the extent that such other embodiments are so drawn, it is intended that they shall fall within the ambit of protection provided by the claims herein.

Having described the invention in the foregoing description and drawings in such a clear and concise manner that those skilled in the art may readily understand and practice the invention, that which is claimed is:

1. In a bed having a mattress and a frame for supporting said mattress, the improvement comprising:
   gentle restraining means for restraining a non-violent person in a generally supine position on a mattress, said gentle restraining means comprising;
   a resilient covering to be yieldably stretchingly drawn over a person lying on said mattress; and
   coupling means for coupling said resilient covering to said mattress to yieldingly restrain a person, over which said covering is drawn, to said mattress;
   said resilient covering being comprised of a resilient, open mesh material through which air and water vapor may readily pass so as to prevent heat entrapment about the body of a person over which said resilient covering may be drawn;
   said coupling means comprises:
   a base positioned beneath said mattress; walls rising from said base to at least partially encompass two sides and a foot of said mattress; and
   releasable coupling means coupling said walls to the sides of said resilient covering.

2. The improvement of claim 1 further comprising frame coupling means coupled to said base for coupling said base to said frame without increasing the level of restraint applied to a person on said mattress over whom said resilient covering is drawn.

3. The improvement of claim 2 wherein said coupling means comprises means for releasedly coupling said base to said frame.

4. Gentle restraining means for restraining a non-violent person in a generally supine position on a mattress, said gentle restraining means comprising;
   a resilient covering to be yieldably stretchingly drawn over a person lying on said mattress; said resilient covering being comprised of a resilient, open mesh material through which air and water vapor may readily pass so as to prevent heat entrapment about the body of a person over which said resilient covering may be drawn;
   a base positioned beneath said mattress; walls rising from said base to at least partially encompass two sides and a foot of said mattress; and
   releasable coupling means coupling said walls to the sides of said resilient covering.

5. The gentle restraint of claim 4 further comprising:
   a frame supporting said mattress; and
   frame coupling means coupled to said base for coupling said base to said frame without increasing the level of restraint applied to a person on said mattress over whom said resilient covering is drawn.

6. The gentle restraint of claim 5 wherein said frame coupling means comprises means for releasedly coupling said base to said bed frame.

7. In a bed having a mattress and a frame for supporting said mattress, the improvement comprising:
   gentle restraining means for restraining a non-violent person in a generally supine position on said mattress, said gentle restraining means comprising;
   a resilient covering to be yieldably stretchingly drawn over a person lying on said mattress; said resilient covering being comprised of a resilient, open mesh material through which air and water vapor may readily pass so as to prevent heat entrapment about the body of a person over which said resilient covering may be drawn;
   a base positioned beneath said mattress; walls rising from said base to at least partially encompass two sides and a foot of said mattress; and
   releasable coupling means coupling said walls to the sides of said resilient covering.

8. The improvement of claim 7 further comprising:
   frame coupling means coupled to said base for coupling said base to said frame without increasing the level of restraint applied to a person on said mattress over whom said resilient covering is drawn.

9. The improvement of claim 8 wherein said frame coupling means comprises means for releasedly coupling said base to said bed frame.

* * * * *